(12) United States Patent
Priewe

(10) Patent No.: US 8,579,990 B2
(45) Date of Patent: Nov. 12, 2013

(54) TISSUE REPAIR DEVICES OF RAPID THERAPEUTIC ABSORBENCY

(75) Inventor: Joerg Priewe, Krummbogen (DE)

(73) Assignee: Ethicon, Inc., Somerville, NJ (US)

( * ) Notice: Subject to any disclaimer, the term of this patent is extended or adjusted under 35 U.S.C. 154(b) by 258 days.

(21) Appl. No.: 13/075,531

(22) Filed: Mar. 30, 2011

(65) Prior Publication Data
US 2012/0253472 A1 Oct. 4, 2012

(51) Int. Cl.
*A61F 2/02* (2006.01)
(52) U.S. Cl.
USPC .................................... 623/23.72
(58) Field of Classification Search
USPC ............ 606/151; 623/1.13, 1.39, 1.46, 23.72; 600/37
See application file for complete search history.

(56) References Cited

U.S. PATENT DOCUMENTS

| | | | |
|---|---|---|---|
| 5,614,284 A | 3/1997 | Kranzler et al. |
| 6,319,264 B1 | 11/2001 | Törmälä et al. |
| 6,398,814 B1 | 6/2002 | Paasimaa et al. |
| 6,875,386 B1 | 4/2005 | Ward et al. |
| 2003/0017775 A1 | 1/2003 | Sowinski et al. |
| 2003/0204270 A1 | 10/2003 | Berman et al. |
| 2005/0261780 A1 | 11/2005 | Heino et al. |
| 2006/0224242 A1 | 10/2006 | Swords et al. |
| 2007/0299542 A1 | 12/2007 | Mathisen et al. |
| 2009/0004455 A1 | 1/2009 | Gravagna et al. |
| 2009/0152766 A1 | 6/2009 | Rousseau et al. |
| 2012/0046587 A1 | 2/2012 | Wild et al. |

FOREIGN PATENT DOCUMENTS

| | | |
|---|---|---|
| EP | 1237588 B1 | 12/2004 |
| EP | 1541183 A1 | 6/2005 |
| EP | 1558173 A1 | 8/2005 |
| EP | 1558173 B1 | 2/2008 |
| EP | 1541183 B1 | 8/2009 |
| WO | 01/85248 | 11/2001 |
| WO | WO 03041613 A1 | 5/2003 |
| WO | WO 03099160 A1 | 12/2003 |
| WO | WO 2010093333 A1 | 8/2010 |
| WO | 2010/124844 | 11/2010 |

OTHER PUBLICATIONS

Yoon Jeong Park et al.,"Porous poly(L-lactide) membranes for guided tissue regeneration and controlled drug delivery: membrane fabrication and characterization" Journal of Controlled Release 43 (1997) 151-160.

*Primary Examiner* — Melanie Tyson
(74) *Attorney, Agent, or Firm* — E. Richard Skula

(57) ABSTRACT

Novel implantable tissue repair medical devices are disclosed. The devices have a central fabric member having anti-adhesion films on both opposed sides. The films have pores, and are arranged such that the pores on the opposed films are offset. The devices are useful in hernia repair procedures.

25 Claims, 2 Drawing Sheets

TISSUE REPAIR DEVICES OF RAPID THERAPEUTIC ABSORBENCY

FIELD OF THE INVENTION

The present invention is directed to soft tissue repair devices capable of minimizing tissue adhesion between adjacent or opposing tissue surfaces, more particularly such soft tissue repair devices capable of rapidly absorbing active agents in an operating room environment prior to implantation.

BACKGROUND OF THE INVENTION

Tissue repair or reinforcing implants, such as meshes, may be designed to enable tissue in-growth on one side (e.g., by having open pores or interstices) and resist tissue in-growth on the opposing side (e.g., by having a smooth surface such as a film or non-porous layer, conventionally referred to in this art as an adhesion barrier). This is important when the mesh implants are used or implanted in the abdominal area, for example in hernia repair procedures, where adhesion of the peritoneum (i.e., tissue ingrowth) to the implant is desired while tissue in-growth or adhesions on the visceral side is unwanted (i.e., anti-adhesion). Several conventional products are known in this art and commercially available having one basically smooth side which is an adhesion barrier and one porous or rough side for tissue in-growth. The products may be completely absorbable, completely non-absorbable, or partially absorbable and partially non-absorbable. The products may be composites of multiple mesh layers and adhesion resistant barriers. Certain implants are ready for use out of the package (e.g., Proceed® Hernia Mesh, Gore DualMesh®, and Bard Composix® Mesh) and other mesh implants are required to be pre-soaked for several minutes in water or saline solution prior to implantation in order to swell the adhesion barrier and make the implant sufficiently soft for implantation and placement in the patient (e.g., Sepramesh®; Parietex® Composite).

In certain surgical applications, it is desirable for these implants to deliver a dose of therapeutic or active agent to the tissues surrounding or adjacent to the implant. To achieve this, the implant may be preloaded by coating or otherwise impregnating with the desired active agent by the manufacturer prior to packaging. However, preloading an implant with an active agent can be difficult. In addition, the amount of active agent that can be added to the implant is limited unless the active agent is delivered in a controlled release manner by the implant for controlled release to the adjacent tissues. To enable the release of stored active agent on both sides of an implant, the implant's active agent reservoir must have fluid communication with each side of the implant. In the case of an implant consisting of a mesh contained between opposed outer film layers, this can be made possible by including pores within the films on both sides of the mesh. However, providing such pores may allow tissue-to-tissue contact through the pores located in the films in those areas where the films are laminated to each other and the pores are in alignment. Tissue-to-tissue contact will encourage or permit unwanted tissue adhesions. If pores are present in only one film layer of the implant, the therapeutic fluid may not be effectively exposed to the side without any pores. It is also believed that having pores on only one side will limit tissue fluid flow between the two sides of the implant. This may result in seroma formation.

A conventional way to deliver active agents in conjunction with implanted medical devices is for the surgeon or assistant to dip or soak the medical device in a solution of the active agent prior to implantation. As an example, dipping surgical hernia mesh film constructs in active agent solutions is important to provide an active-loaded mesh that may also be placed in contact with the viscera to prevent adhesions. In other applications there may be a need to place the fabric in contact with the vaginal wall (e.g., a pelvic mesh) or in contact with the urethra such as with the GYNECARE® TVT system from Ethicon, Inc., wherein a perforated film assembly could be beneficial to prevent erosion of structures like the bladder, vaginal wall, etc. by a part of the implant. Currently marketed and commercially available products that are coated with collagen films (e.g., Parietex®Composite (PCO) MESH) have to be incubated for 5-10 minutes in a solution of active agent, which is relatively time consuming task to perform when in an operating room (OR) setting and while the patient is under anesthesia during a procedure. A further drawback with current commercially available products is that the active agent coatings are very sensitive to mechanical forces during handling in the operating room, and using forceps to manipulate or place the implants can easily destroy such coatings and may lead to disintegration of the product. Certain commercially available mesh composite implants such as Composix® mesh, have a polypropylene mesh with an ePTFE layer on one side of the mesh. Since both polypropylene and ePTFE both do not accept hydrophilic liquids very well, it is anticipated that the delivery of such meshes along with a coating solution of active ingredient through a trocar to the surgical site would be difficult.

WO2003041613 A1 describes meshes having two synthetic polymer films on each side, wherein the films are glued or welded in the pores of the mesh together; neither perforated pore-containing films on both sides nor offset pore-containing films are described.

EP1237588 B1 describes a non-absorbable mesh implant covered on one side with an absorbable film made from natural (hyaluronic acid) or natural-derived (CMC) materials which may have pores, and in between an adhesive such as a polylactide co-polymer. A drug may be incorporated in any portion of the prosthesis to provide for controlled release of the drug into the body.

WO2003099160 A1 describes knobbed films that may be present on both sides of a fabric implant, wherein both films can have holes that are arranged in a pattern. Filling the knobs with an active agent is taught, however dipping or filling the area outside the knobs is not indicated.

EP 1541183 A1 describes a mesh having absorbable polymer films with two different absorption times. US20030017775 A1 describes a composite intraluminal prosthesis which is preferably used as a vascular prosthesis and includes a layer of ePTFE and a layer of textile material, which are secured together by an elastomeric bonding agent. The ePTFE layer includes a porous microstructure defined by nodes interconnected by fibrils. The adhesive bonding agent is preferably applied in solution so that the bonding agent enters the pores of the microstructure of the ePTFE.

There is a need in this art for tissue implant devices that offer advantages over the tissue devices of the prior art, including providing a device that permits rapid absorption of active agents while providing tissue separating properties at least for a certain period of time. In particular, tissue implants are needed that are well suited to fast dip coating processes for providing active implants with effective amounts of active agents in a quick and efficient manner, particularly for dipping in the operating room. Also needed are fast, dippable mesh-laminate implants suitable for an inline process (pulling through a coating bath), wherein the impregnation time of the active agent into the mesh implant is reduced.

SUMMARY OF THE INVENTION

Accordingly, novel tissue repair implant medical devices are disclosed. The tissue implant medical device of the present invention has a tissue repair member having a plurality of member openings or pores and is preferably a fabric such as a mesh. The repair member has opposed first and second sides. A first polymer film, having first film pores, is mounted on the first side of the member. A second polymer film, having second film pores, is mounted on the second side of the member. The first film pores are not in alignment with the second film pores, that is, the pores are offset, such that tissue-to-tissue contact is substantially prevented.

Yet another aspect of the present invention is a method of repairing a tissue defect, utilizing the above-described tissue repair implant devices.

Still yet another aspect of the present invention is a combination of the above-described tissue repair implant device and an active agent.

The tissue repair devices of the present invention have many advantages. One advantage of the devices of the present invention is to allow an active agent-containing liquid to impregnate the repair fabric and the films in a short period of time, while not exposing facing or adjacent tissue to direct contact once implanted, thereby minimizing the possibility of tissue adhesions. The devices of this invention are particularly well suited to dipping into solutions of active agents, whether in a batch process (such as in an operating room environment) or through a manufacturing process, and demonstrate fast absorption of liquids.

DETAILED DESCRIPTION OF THE INVENTION

Figure 1:
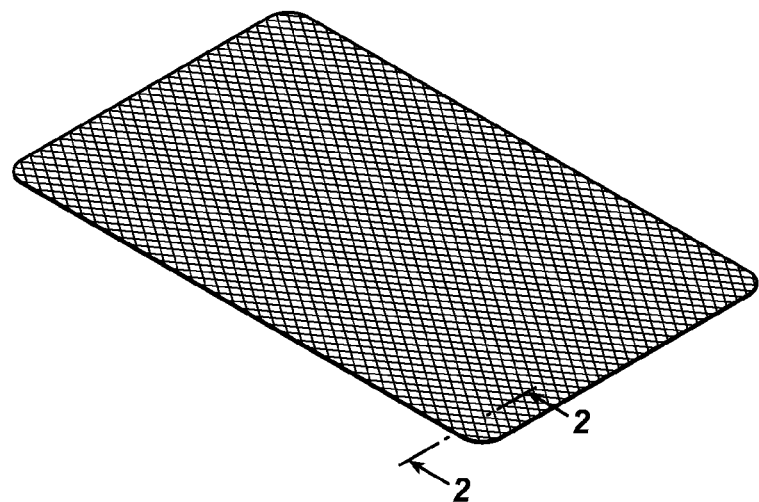
FIG. 1 is a perspective view of an embodiment of a tissue repair device of the present invention.

The implantable tissue repair medical devices of the present invention as described herein consist of a composite of a tissue repair fabric member and porous adhesion barrier films mounted on opposed outer sides of the tissue repair fabric. Both of the films have pores, such that the tissue repair devices can be easily and quickly dipped, independent of the size of the device and the manner in which it is placed, in a dipping bath, i.e., horizontally or vertically. Due to the non-overlapping or nonaligned orientation of the pores in the opposing films of the devices of the present invention (i.e., offset pores), the devices may be placed in contact with viscera with little concern since the aforementioned pore orientation substantially or completely prevents tissue-to-tissue contact and allows at the same time tissue-to-mesh contact on both sides (good ingrowth). Also, less seroma formation is expected (and hence less infection), due to improved fluid flow through the implant.

Surgical repair fabrics suitable for use as the intermediate or middle layer of the tissue repair devices of the present invention include conventional meshes, woven fabrics, and tapes for surgical applications. Other fabrics or materials include perforated condensed ePTFE films and nonwoven fabrics having pore sizes of at least one millimeter.

The fabrics will have open pores with a size of at least 1 mm. By "open pores" is meant openings that extend from one side of the fabric to the opposed side, providing a pathway through the fabric.

Depending upon the intended use of the tissue repair device, a biocompatible long-term-stable polymer may be used to manufacture the fabric repair member. By a long-term-stable polymer is meant a non-resorbable biocompatible polymer, or a bioabsorbable polymer which absorbs or degrades slowly, for example which possesses at least 50% of its original tearing strength in vivo 60 days after implantation. The latter group includes substances such as polyamides, which generally are regarded as resistant, as they are not designed as resorbable materials, but are attacked over time by body tissue and tissue fluids. Preferred materials for the fabric repair member include polyhydroxy acids, polylactides, polyglycolides, polyhydroxy butyrates, polyhydroxy valeriates, polycaprolactones, polydioxanones, synthetic and natural oligo- and polyamino acids, polyphosphazenes, polyanhydrides, polyorthoesters, polyphosphates, polyphosphonates, polyalcohols, polysaccharides, polyethers, polyamides, aliphatic polyesters, aromatic polyesters, copolymers of polymerizable substances thereof, resorbable glasses.

Particularly preferred materials for the fabric repair member include polypropylene and mixtures of polyvinylidene fluoride and copolymers of vinylidene fluoride and hexafluoropropene, PTFE, ePTFE, and cPTFE, but other conventional biocompatible materials are also useful. The fabric repair members may be constructed from monofilaments, multifilaments, or combinations thereof.

The fabric repair member may contain, in addition to a long-term stable polymer, a resorbable polymer (i.e., bioabsorbable or biodegradeable). The resorbable and the long-term stable polymer preferably contain monofilaments and/or multifilaments. The terms resorbable polymers and bioabsorbable polymers are used interchangeably herein. The term bioabsorbable is defined to have its conventional meaning. Although not preferred, the fabric repair member may be manufactured from a bioabsorbable or bioabsorbable polymers without any long-term stable polymers.

The films that are used to manufacture the tissue repair implant devices of the present invention will have a thickness that is sufficient to effectively prevent adhesions from forming The thickness will typically range from about 1 µm to about 500 µm, and preferably from about 5 µm to about 50 µm. The films suitable for use as the first and second films of the tissue repair devices of the present invention include both bioabsorbable and non-absorbable films. The films are preferably polymer-based and may be made from various conventional biocompatible polymers. Non-resorbable or very slowly resorbable substances include polyalkenes (e.g. polypropylene or polyethylene), fluorinated polyolefins (e.g. polytetrafluoroethylene or polyvinylidene fluoride), polyamides, polyurethanes, polyisoprenes, polystyrenes, polysilicones, polycarbonates, polyarylether ketones (PEEKs), polymethacrylic acid esters, polyacrylic acid esters, aromatic polyesters, polyimides as well as mixtures and/or co-polymers of these substances. Also useful are synthetic bioabsorbable polymer materials for example, polyhydroxy acids (e.g. polylactides, polyglycolides, polyhydroxybutyrates, polyhydroxyvaleriates), polycaprolactones, polydioxanones, synthetic and natural oligo- and polyamino acids, polyphosphazenes, polyanhydrides, polyorthoesters, polyphosphates, polyphosphonates, polyalcohols, polysaccharides, polyethers. However, naturally occurring materials such as collagen, gelantin or natural-derived materials such as bioabsorbable Omega 3 fatty acid crosslinked gel films or oxygenized regenerated cellulose (ORC) can also be used.

The films used in the tissue repair devices of the present invention may cover the entire outer surfaces of the repair fabric member or a part thereof. In some cases, it is beneficial to have films overlapping the borders of the repair fabric. The term border used herein means a peripheral edge or central edge if there is a hole in the mesh, e.g., for receiving an anatomical structure like the bowel for treating or preventing parastomal hernia or the spermic cord.

The porous films used to construct the devices of the present invention will have open pores. Perforated or porous films may be prepared using conventional processes such as mechanical cutting or punching, by applying energy such as laser light, ultrasound, microwave, heat or corona/plasma. Chemical etching or injection molding molding processes can also be used. Conventional foaming processes including lyophilization may also be used to create the open porous structure.

The pores in the films may be made in the form of multiple slits or incisions without cutting out or removing material from the film, or may have a certain length and width or diameter resulting from the removal of material from the film, or may be openings resulting from the absence of polymeric material at locations within the film. The pores may have various geometric configurations including circular, oval, rectangular, diamond-shaped, square, triangular, polygonal, irregular, combinations thereof and the like. It is particularly preferred that the pores are bore holes extending through the film having a circular cross-section.

The films may be perforated before or after assembling the device, or the films may be manufactured in such a manner that they contain pores. However, it will be appreciated by those skilled in the art that precautions have to taken to prevent damage the fabric member or the second film when perforating an assembled device.

For ease of manufacturing during assembling and a desired wetability with aqueous coatings (i.e., liquid has to go in/air has to go out), the perforation/pore size should typically be at least 0.2 mm to 5 cm, preferably 0.5 to 7 mm, most preferably 1 to 5 mm at least in one direction. As previously mentioned, the pores can have different sizes and shapes. Additionally, depending on the manufacturing technique, the edges of the film pores may be smooth or rough. Also, the edges of the pores may be embossed and rounded or beveled.

The films can be joined together in various conventional manners, for example by sewing, gluing, welding, and laminating. The joining/connection can be about the periphery, in the center region, or over the whole assembly as a point linear or overall connection, making sure that the pores of the top and bottom films are substantially offset.

The films can be connected to each other and/or to the repair fabric member in variety of different conventional ways, e.g., sewn, embroidered, bonded (including by thermal means) in partial regions (e.g., in points or along lines or strips, such as the peripheral edge), or welded thermally including ultrasonically. The welding techniques also include, in the wider sense, thermal deformation of at least one of the films (below the melting point of one film). The implant can optionally have embroidered structures designed as reinforcements, e.g. rib-like structures.

Particularly preferred for the devices of the present invention is a film-to-film connection using heat lamination techniques, optionally by using an additional biocompatible melt glue such as polydioxanone as a relatively low melting bioabsorbable polymer. Other soluble polymers such as polylactide, polycaprolactone or copolymers thereof might be used as solvent glues. Reactive glues like cyanoacrylates or isocyanantes or oxiranes may also be used if biocompatible.

Figure 2:
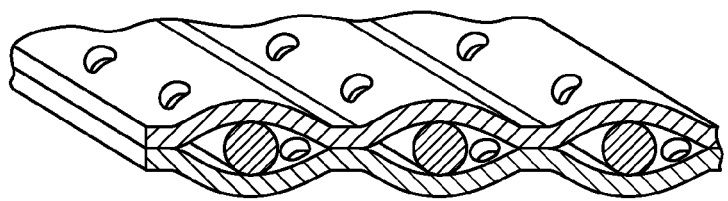
FIG. 2 illustrates a magnified partial cross-section of the tissue repair device of FIG. 1 along Viewline 2-2.

Referring now to FIGS. 1 and 2, a tissue repair implant device 1 of the present invention is seen. The device 1 is seen to have a central or middle fabric member 20. Member 20 is seen to be a substantially flat mesh knitted from fibers 22. The member 20 is seen to have a plurality of mesh openings or mesh pores 25 formed between the fibers 22. The member 20 has opposed outer sides 28. The device 1 is also seen to have first and second porous adhesion barrier films 10 and 30 mounted, respectively, to the fabric member 20 on opposed sides 28. In this embodiment of the tissue repair device of the present invention, the films 10 and 30 are connected together through the mesh openings or mesh pores 25. The first film 10 is seen to have film pores 12 extending therethrough, while the second film 30 has film pores 32 extending therethrough. The pores 12 and the pores 32 are arranged to be offset so as to not be in alignment, thereby not providing a direct pathway between opposed pores 12 and 32.

The term active agents includes but is not limited to therapeutic agents. The selection of active agents that can be used in combination with medical devices of the present invention depends upon the desired patient benefit intended to be derived. For example, it may be advantageous to provide an implant of the present invention that has at least one biologically active or therapeutic ingredient which can optionally be released locally after the implantation. Substances which are suitable as active or therapeutic agents may be naturally occurring or synthetic, and include and are not limited to, for example, antibiotics, antimicrobials, antibacterials, antiseptics, chemotherapeutics, cytostatics, metastasis inhibitors, antidiabetics, antimycotics, gynecological agents, urological agents, anti-allergic agents, sexual hormones, sexual hormone inhibitors, haemostyptics, hormones, peptide-hormones, antidepressants, vitamins such as Vitamin C, antihistamines, naked DNA, plasmid DNA, cationic DNA complexes, RNA, cell constituents, vaccines, cells occurring naturally in the body or genetically modified cells. The active or therapeutic agent may be present in various forms including in an encapsulated form or in an adsorbed form. With such active agents, the patient outcome may be improved or a therapeutic effect may be provided (e.g., better wound healing, or inflammation inhibition or reduction).

One preferred class of active agents is antibiotics that include such agents as gentamicin or ZEVTERA™ (ceftobiprole medocaril) brand antibiotic (available from Basilea Pharmaceutica Ltd., Basel Switzerland). Other active agents that may be used are highly effective, broad band antimicrobials against different bacteria and yeast (even in the presence of bodily liquids) such as octenidine, octenidine dihydrochloride (available as active ingredient in Octenisept® disinfectant from Schülke & Mayr, Norderstedt, Germany as), polyhexamethylene biguanide (PHMB) (available as active ingredient in Lavasept® from Braun, Switzerland), triclosan, copper (Cu), silver (Ag), nanosilver, gold (Au), selenium (Se), gallium (Ga), taurolidine, N-chlorotaurine, alcohol based antiseptics such as Listerine® mouthwash, N α-lauryl-L-arginine ethyl ester (LAE), myristamidopropyl dimethylamine (MAPD, available as an active ingredient in SCHER- CODINE™ M), oleamidopropyl dimethylamine (OAPD, available as an active ingredient in SCHERCODINE™ O), and stearamidopropyl dimethylamine (SAPD, available as an active ingredient in SCHERCODINE™ S), fatty acid monoesters, and most preferably octenidine dihydrochloride (hereinafter referred to as octenidine), Taureolidine, and PHMB.

One preferred class of active agents are local anesthetics that includes such agents as: Ambucaine, Benzocaine, Butacaine, Procaine/Benzocaine, Chloroprocaine, Cocaine, Cyclomethycaine, Dimethocaine/Larocaine, Etidocaine, Hydroxyprocaine, Hexylcaine, Isobucaine, Paraethoxycaine, Piperocaine, Procainamide, Propoxycaine, Procaine/Novocaine, Proparacaine, Tetracaine/Amethocaine, Lidocaine, Articaine, Bupivacaine, Dibucaine, Cinchocaine/Dibucaine, Etidocaine, Levobupivacaine, Lidocaine/Lignocaine, Mepivacaine, Metabutoxycaine, Piridocaine, Prilocalne, Propoxycaine, Pyrrocaine, Ropivacaine, Tetracaine, Trimecaine, Tolycaine, combinations thereof, e.g., Lidocaine/prilocalne (EMLA) or naturally derived local anesthetics including Saxitoxin, Tetrodotoxin, Menthol, Eugenol and pro-drugs or derivatives thereof.

In some instances, the active or therapeutic agent is provided in a solution. The solution may comprise any suitable solvent compatible with the selected active ingredient. The solution may be water-based and may contain at least one of the following additional conventional ingredients: a surface active agent, a polymer, protein or dye. Polymers are used to adjust the release rate. Depending on the active agent and release required, polymer solvent mixtures for coatings might be advantageous.

Additionally, a contrast agent may be incorporated into the devices of the present invention. Such a contrast agent may be a biocompatible dye to create a visual marker as described in EP1392198B1 which is incorporated by reference or an agent such as a gas or gas creating substance for ultrasound contrast or MRI contrast, such as metal complexes like GdDTPA or superparamagnetic nanoparticles (Resovist™ or Endorem™) as taught in the EP 1324783 B1, which is incorporated by reference. X-Ray visible substances might be included as shown in the EP1251794B1 (incorporated by reference) including pure zirconium dioxide, stabilized zirconium dioxide, zirconium nitride, zirconium carbide, tantalum, tantalum pentoxide, barium ulphate, silver, silver iodide, gold, platinum, palladium, iridium, copper, ferric oxides, not very magnetic implant steels, non-magnetic implant steels, titanium, alkali iodides, iodated aromatics, iodated aliphatics, iodated oligomers, iodated polymers, alloys of substances thereof capable of being alloyed. The contrast agents may be included in or on the mesh, or in or on the films.

Additionally, swelling or gel forming substances might be added to the mesh and/or films. This has the advantage of improving the uptake of the dipping solution. The substances include proteins such as collagen or gelatin, surfactants such as PPO-PEO block copolymers (Pluronics), polysorbates such as polysorbate 20, 40, 60, 65, 80 (Tweens), or spans like Span 20 (Sorbitan monolaurate), Span 40 (Sorbitan monopalmitate), Span 60 (Sorbitan monostearate), Span 65 (Sorbitan tristearate), Span 80 (Sorbitan monooleate), phospholipids, hydophilic natural or synthetic polymers such as alginate, dextrane, chitosane, carracen, PEG, PVA, PVP, CMC, HES.

Hydrogel forming polymers may be obtained upon the polymerization or polyaddition or polycondensation containing at least one of the substances selected from the following group: polymerized hydroxyethyl methacrylate (HEMA); polymerized hydroxypropyl methacrylate (HPMA); polymerized a-methacryloyl-o-methoxy polyethylene glycol; polymerized polyethylene glycol-bisacrylate; resorbable prepolymers of type A-B-C-B-A with A=acryl or methacryl groups, B=hydrolytically splittable and containing polymers of lactide, glycolide, 2-hydroxybutyric acid, 2-hydroxyvaleriac acid, trimethylene carbonate, polyorthoesters, polyanhydrides, polyphosphates, polyphosphazenes and/or polyamides and/or copolymers thereof, and C=hydrophilic polymers, in particular polyethylene glycol (PEG), polyvinyl alcohol (PVA), polyvinyl pyrrolidone (PVP), poly N-isopro-lyacrylamide (PNiPAAM).

The following examples are illustrative of the principles and practice of the present invention although not limited thereto.

Example 1

Lightweight Mesh Laminated Between Two Porous Monocryl® Films

A lightweight polypropylene mesh having the same knitting structure as Ultrapro® brand mesh available from Ethicon, Inc., Somerville, N.J. U.S.A. but without the absorbable Monocryl® filaments-(poliglecaprone 25) was prepared. This mesh was heat laminated between two film layers. The first film consisted of 20 μm thick poliglecaprone 25 Monocryl® film that was extruded and laminated with an 8 μm thick poly-p-dioxanone (PDS) film. The pre-laminate was laser-cut with 1 mm holes or pores with a hole-to-hole distance of 5 mm. A second laminate layer comprising poliglecaprone 25 Monocryl film having a thickness of _____ was laser cut and pre-cut in the same manner as the first laminate layer above. Both films were placed in such a way that the holes or pores were not in alignment (i.e., offset) and were mounted as opposed outer films on the outer surfaces of the polypropylene mesh. The film mesh construct was laminated in a heat press between several layers of baking paper and chilled between 2 metal plates (30 seconds, 120° C. and chilled for about 30 minutes between metal plates).

An 8×11 cm sample of this laminate was placed horizontally in a dish containing 0.1% (wt/wt) of antibacterial crystal violet aqueous solution as a model antibacterial solution.

The laminated mesh, including the mesh and the films, was completely impregnated with the solution within 10 seconds.

A film laminate having films with no holes or pores of the same size was similarly tested and 1 required a significantly longer time to impregnate. The impregnation time for the film laminates without pores or holes was observed to be about 5-10 minutes or longer.

After drying the coated impregnated mesh laminate it was observed that the film gluing area in the center of the mesh pores is basically free of the antibacterial dye and the mesh and the mesh surrounding area between the films is stained (about 30%-50% of the total area).

Figure 3:
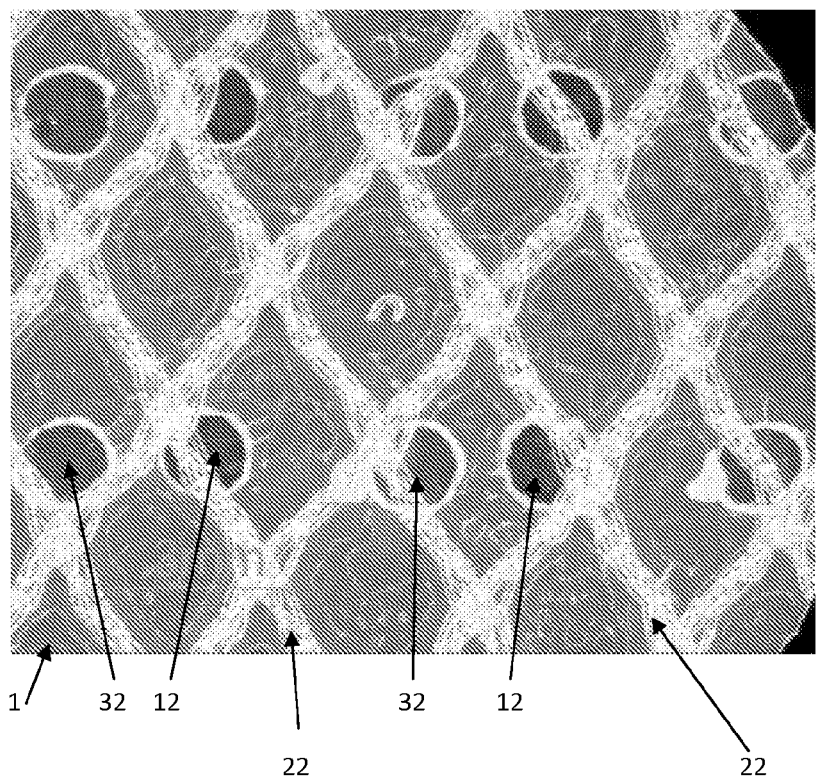
FIG. 3 is a picture of a section of one embodiment of a tissue repair device of the present invention made in accordance with Example 1 showing the relationship of the top film pores in the top porous film to the bottom film pores in the bottom porous film, and central mesh.
Figure 4:
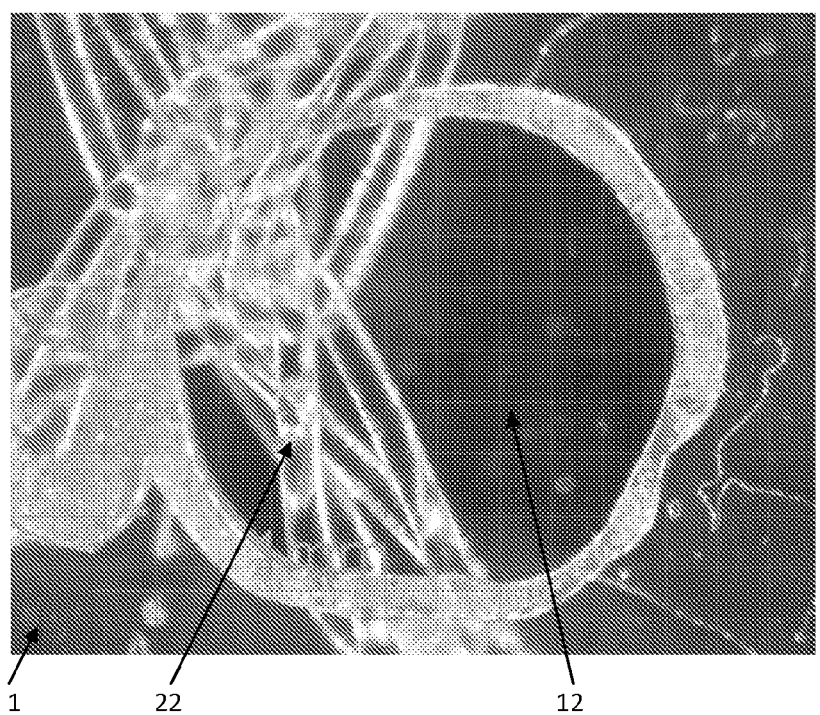
FIG. 4 is an enlarged picture of a pore in a film according to one embodiment of the present invention made in accordance with Example 1.

A picture of a section of one embodiment of a tissue repair device of the present invention made in accordance with this Example 1 is seen in FIG. 3. It shows the relationship of the top film pores in the top porous film to the bottom film pores in the bottom porous film, and a central mesh. FIG. 4 is an enlarged picture of a pore in a film according to one embodiment of the present invention made in accordance with this Example 1.

Example 2

Horizontal Dipping

This example demonstrated the wetting capabilities of the tissue repair devices of the present invention compared with non-porous devices.

Several 8×12 cm laminates with pore-containing films (pore diameter=1 mm, pore spacing=5 mm) were prepared according to Example 1. Several 8×12 cm laminates with nonporous films were prepared according to Example 1 with the exception that nonporous films were used in place of the porous films. The dry weight was determined for the porous and nonporous laminates.

The laminates were placed horizontally into a flat vessel containing 500 ml 0.2% Lavasept solution for 10 seconds (made from a Lavasept concentrate (20% PHMB), Lot 7383M03). The laminates were taken out and slightly shaken, to remove excess of liquid and weight was determined again. Table 1 contains the results of the horizontal dipping experiments.

TABLE 1

HORIZONTAL DIPPING EXPERIMENTS

| Laminate | Dry Weight (Before dipping) [grams] | Wetted Weights (After 10 s dipping) [grams] | Weight increase (%) | Avg increase % | SD % |
|---|---|---|---|---|---|
| 1) Porous | 0.7801 | 2.0006 | 256 | — | — |
| 2) Porous | 0.7707 | 1.9505 | 253 | — | — |
| 3) Porous | 0.8013 | 2.0184 | 252 | 254 | 2 |
| 4) Nonporous | 0.9558 | 1.4962 | 157 | — | — |
| 5) Nonporous | 0.9512 | 1.4957 | 157 | — | — |
| 6) Nonporous | 0.9604 | 1.8926 | 197 | 170 | 23 |

All of the pore-containing laminates appeared to be completely wetted including in between the films. The nonporous laminates were starting to wet between films in the periphery (in particular Laminate 6 was about a quarter wetted between the films after 10 seconds).

The pore-containing laminates had about 70% higher liquid uptake after 10 seconds (170%→254%).

The weight gain of the nonporous laminates seem to be entirely due to liquid on top of the films, while the increase in the pore-containing laminates was additionally due to liquid uptake between the films.

Example 3

Horizontal Dipping in the OR and Handling Properties

Laminates were prepared in accordance with Example 1, but in an 18 cm×14 cm size. Pore-containing and nonporous laminates were placed through a conventional 12 mm trocar inserted through to the abdominal cavity of a swine. The implants were easily movable (sliding) at the intestine and then placed against the abdominal wall. Pore-containing and nonporous laminates were removably self-attaching to the abdominal wall. No instrument was needed to keep them up in place.

The same handling behavior was observed even for 10 second isotonic saline pre-wetted implants.

With the area weights calculated from Table 1 test articles had an attachment force to the abdominal wall greater than their own area weight of 20 mg/cm$^2$ in the case of the dipped perforated film (calculated from 2 g of the 8×11 cm perforated wet implant in tab 1).

The devices of this invention were seen to be useful for adhesion prevention as a film barrier and potential drug delivery carrier in surgical fields such as pelvic, colorectal and plastic surgery.

Example 4

Porous cPTFE Sheet Between 2 Perforated Films

A 10×10 cm Omyra mesh (B. Braun) was laminated according to Example 1 between perforated Monocryl® films at 120° C. for 5 minutes and then chilled down between two cold metal plates for additional 30 minutes. The films were stable laminated within the pores of the mesh, usual handling and bending of the composite implant indicated no delamination. Optical control showed no overlap of the film pores, that is, offset pores.

Example 5

Perforate Film Laminate with Octenidine+Coating Polymer Dip Coating

A 16 cm×16 cm mesh laminate was prepared according to Example 1.

1 kg of a coating solution was prepared containing 1.5 g Octenidine Dihydrochloride+9 g Coating Polymer PEDG/PLLA 60/40 in accordance with Example 5b of commonly-assigned, co-pending patent application Ser. No. 12/609,101 filed on Oct. 30, 3009 (incorporated by reference)+889 g Aceton+100 g deionized water.

The coating solution was purged in a thin and high vertical rectangular coating bath (length ~20 cm, high ~20 cm, with ~2 cm) and the implant sheet dwell time in the bast was about 5 minutes and it was then pulled out with a speed of 3 mm/sec, allowed to dry (about 30 minutes at room temperature/normal pressure and then over night in a vacuum chamber evaporated by an oil pump.), punched into 1.5 cm circles, packaged, and sterilized using a conventional ethylene oxide sterilization process.

After sterilization the disks had a content of 2200 ppm of Octenidine with a standard deviation of 11% between 3 mesh disks.

In an FCS containing *S. aureus* assay the mesh disks showed strong antibacterial activity when incubated for 4 hours in 3 ml bacteria/serum mixture of at least 1 g5 compared to the uncoated control.

Example 6

Surgical Procedure Using the Tissue Repair Implant Devices of the Present Invention A patient with a ventral hernia is prepared for surgery in a conventional manner, and anesthetized in a conventional manner. The ventral hernia repair procedure is performed in the following manner using a tissue repair implant device of the present invention.

LVHR (Laparoscopic Ventral Hernia Repair)

After placing the trocars, setting the pneumoperitoneum, clearing the hernia sack of its contents and lyses of adhesions, the surgeon identifies the size of the hernia defect.

An appropriate-sized mesh (according to the present invention) having a certain overlap to cover the hernia defect is tightly rolled up and passed into the abdomen through a 10 mm or 12 mm port. If needed the mesh is dipped for a few seconds into a vessel containing an active solution such as antibiotics or antiseptics prior to passage through a trocar into the patient.

After the trocar passage the mesh unrolls by itself or unrolls with minimal assistance from an appropriate surgical instrument on the intestine and is moved and positioned to the right place and orientation. Then the mesh is lifted up at the abdominal wall to cover the defect and self attaches or is attached to the abdominal wall. Fixation is performed in a conventional manner using transabdominal sutures or staples.

Although this invention has been shown and described with respect to detailed embodiments thereof, it will be understood by those skilled in the art that various changes in form and detail thereof may be made without departing from the spirit and scope of the claimed invention.

What is claimed is:

1. A tissue implant medical device, comprising:
   a tissue repair member having a plurality of member pores, the repair member having opposed first and second sides;
   a first polymer film, having first film pores, the first polymer film mounted to the first side of the member; and,
   a second polymer film, having second film pores, the second polymer film mounted to the second side of the repair member, wherein the first film pores are not in alignment with the second film pores.

2. The medical device of claim 1, further comprising an active agent.

3. The medical device of claim 2, wherein the active agent is selected from the group consisting of, antibiotics, chemotherapeutics, cytostatics, metastasis inhibitors, antidiabetics, antimycotics, antimicrobials, antibacterials, vitamins, gynaecological agents, urological agents, anti-allergic agents, sexual hormones, sexual hormone inhibitors, local anesthetics, haemostyptics, hormones, peptide hormones, vitamins, antidepressants, anti-histamines, naked DNA, plasmid DNA, cationic DNA complexes, RNA, cell constituents, vaccines, cells occurring naturally in the body, genetically modified cells and combinations thereof.

4. The medical device of claim 3, wherein the active agent is an antimicrobial selected from the group consisting of octenidine, PHMB, triclosan, copper, silver, nanosilver, gold, selenium, gallium, taurolidine, cyclotaurolidine, N-chlorotaurine, alcohol, LAE, MAPD, OAPD, and mixtures thereof.

5. The medical device of claim 4, wherein the antimicrobial is triclosan.

6. The medical device of claim 4, wherein the antimicrobial is octenidine.

7. The medical device of claim 4, wherein the antimicrobial is PHMB.

8. The medical device of claim 1, wherein the tissue repair member is a fabric.

9. The medical device of claim 8, wherein the tissue repair fabric is selected from the group consisting of meshes, woven fabrics, nonwoven fabrics and tapes.

10. The medical device of claim 9, wherein the tissue repair fabric comprises a mesh.

11. The medical device of claim 1, wherein the tissue repair member comprises a biocompatible nonabsorbable polymer selected from the group consisting of polyalkenes, polypropylene, polyethylene, fluorinated polyolefins, polytetrafluoroethylene, polyvinylidenefluoride, polyamides, polyurethanes, polyisoprenes, polystyrenes, polysilicones, polycarbonates, polyaryletherketones, polymethacrylates, polyacrylates, aromatic polyesters, polyimides, cellulose, copolymers of polymerisable substances thereof.

12. The medical device of claim 1, wherein the tissue repair member comprises a bioabsorbable polymer selected from the group consisting of polyhydroxy acids, polylactides, polyglycolides, polyhydroxybutyrates, polyhy droxyvaleriates, polycaprolactones, polydiaxanones, synthetic and natural oligo- and polyaminoacids, polyphosphazenes, polyanhydrides, polyorthoesters, polyoxaester, polyphosphates, polyphosphonates, polyalcohols, polysaccharides, polyethers, resorbable glasses, copolymers of polymerizable substances thereof.

13. The medical device of claim 1 wherein the first and second films comprise a biocompatible nonabsorbable polymer selected from the group consisting of polyolefins, polyester, Nylon, Teflon, polyvinidenefluoride, and cellulose.

14. The medical device of claim 1 wherein the first and second films comprise a biocompatible bioabsorbable polymer selected from the group consisting of polyhydroxy acids, polylactides, polyglycolides, polyhydroxy butyrates, polyhydroxy valeriates, polycaprolactones, polydioxanones, synthetic and natural oligo- and polyamino acids, polyphosphazenes, polyanhydrides, polyorthoesters, polyphosphates, polyphosphonates, polyalcohols, polysaccharides, polyethers, polyamides, aliphatic polyesters, aromatic polyesters, copolymers of polymerizable substances thereof, and resorbable glasses.

15. The medical device of claim 1, wherein the film pores of the first and second polymer films have a size ranging from about 0.1 mm to about 5 mm.

16. The medical device of claim 1, wherein the films have a thickness of about 5 µm to about 50 µm.

17. The medical device of claim 1, wherein the tissue repair member comprises monofilament fibers.

18. The medical device of claim 1, wherein the tissue repair member comprises multifilament fibers.

19. The medical device of claim 1, additionally comprising a polymeric coating.

20. The medical device of claim 1, wherein the pores have a substantially circular cross-section.

21. The medical device of claim 1, wherein the film pores of the first and second polymer films comprise slits.

22. A method of repairing a tissue defect, comprising the steps of:
   inserting a tissue repair implant device adjacent to a tissue defect, wherein the device comprises:
   a tissue repair member having a plurality of member pores, the repair member having opposed first and second sides;
   a first polymer film, having first film pores, the first polymer film mounted to the first side of the member; and,
   a second polymer film, having second film pores, the second polymer film mounted to the second side of the repair member,
   wherein the first film pores are not in alignment with the second film pores; and,
   securing the repair device to the tissue defect.

23. The method of claim 22, additionally comprising the step of immersing the device in a solution containing an active agent prior to inserting the tissue repair device.

24. The combination, comprising:
   a) A tissue implant medical device, comprising:
   a tissue repair member having a plurality of member pores, the repair member having opposed first and second sides;
   a first polymer film, having first film pores, the first polymer film mounted to the first side of the member; and,
   a second polymer film, having second film pores, the second polymer film mounted to the second side of the repair member,
   wherein the first film pores are not in alignment with the second film pores; and,
   b) An active agent.

25. The combination of claim 24, wherein the active agent is in a solution.

* * * * *